United States Patent
Baumann (10) Patent No.: US 9,724,287 B2
(45) Date of Patent: Aug. 8, 2017

(54) OPTIMIZED SKINCARE REGIMENS FOR CHANGING THE GENETIC SKIN TYPE TO THE IDEAL SKIN TYPE—OILY, RESISTANT, NON-PIGMENTED AND TIGHT SKIN

(71) Applicant: Leslie S. Baumann, Miami Beach, FL (US)

(72) Inventor: Leslie S. Baumann, Miami Beach, FL (US)

(73) Assignee: METABEAUTY, INC., Miami, FL (US)

( * ) Notice: Subject to any disclaimer, the term of this patent is extended or adjusted under 35 U.S.C. 154(b) by 0 days.

(21) Appl. No.: 14/997,266

(22) Filed: Jan. 15, 2016

(65) Prior Publication Data

US 2016/0128925 A1    May 12, 2016

Related U.S. Application Data (63) Continuation-in-part of application No. 14/025,546, filed on Sep. 12, 2013, now abandoned, which is a continuation of application No. 11/283,511, filed on Nov. 21, 2005, now abandoned.

(60) Provisional application No. 60/629,320, filed on Nov. 19, 2004.

(51) Int. Cl.
*A61Q 19/00* (2006.01)
*A61K 8/67* (2006.01)
*A61Q 19/02* (2006.01)
*A61Q 19/08* (2006.01)
*A61K 8/368* (2006.01)
*A61Q 19/10* (2006.01)

(52) U.S. Cl.
CPC ............. *A61K 8/676* (2013.01); *A61K 8/368* (2013.01); *A61K 8/671* (2013.01); *A61Q 19/00* (2013.01); *A61Q 19/005* (2013.01); *A61Q 19/008* (2013.01); *A61Q 19/02* (2013.01); *A61Q 19/08* (2013.01); *A61Q 19/10* (2013.01)

(58) Field of Classification Search
None
See application file for complete search history.

(56) References Cited

PUBLICATIONS

Eucerin: About skin/Daily skincare routine for the face (accessed at www.eucerin.sg/about-skin/skin-treatment/daily-routine-for-face, on Feb. 21, 2017 (available online Dec. 20, 2014).*

* cited by examiner

*Primary Examiner* — Robert A Wax
*Assistant Examiner* — Melissa Mercier
(74) *Attorney, Agent, or Firm* — Louis C. Paul & Associates, PLLC (57) ABSTRACT

Methods of improving (i.e., changing) the skin of a patient or consumer who does not have sensitive, dry, very oily, pigmented and/or wrinkle-prone skin to slightly oily, resistant non-pigmented and tight skin.

8 Claims, 1 Drawing Sheet

OPTIMIZED SKINCARE REGIMENS FOR CHANGING THE GENETIC SKIN TYPE TO THE IDEAL SKIN TYPE—OILY, RESISTANT, NON-PIGMENTED AND TIGHT SKIN

CROSS-REFERENCE TO RELATED APPLICATIONS

This application is a continuation-in-part of pending, U.S. patent application Ser. No. 14/025,546 (filed on Sep. 12, 2013), which is a continuation of U.S. patent application Ser. No. 11/283,511 (filed on Nov. 21, 2005), which claims the benefit of prior U.S. Provisional Patent Application 60/629,320 (filed Nov. 19, 2004). The benefit of priority to the above-listed applications is claimed, and the entire contents of those applications are hereby incorporated by reference.

FIELD OF INVENTION

The present invention relates to skincare regimens for changing skin to oily, resistant, non-pigmented and tight skin.

BACKGROUND OF THE INVENTION

The vast majority of consumers, as well as physicians, treat skin conditions based on whether the skin is considered oily, dry or, sometimes "combination" (i.e., both oily and dry). Additionally, selection of a skin treatment regimen is sometimes made based on a non-specific assessment of whether the skin is "sensitive." As discussed below, these oversimplifications often result in skin treatment that is ineffectual; and, not uncommonly, worsening of the condition being treated.

Not only are there differing degrees of oiliness and dryness—ranging from very oily to slightly oily, slightly dry or very dry, but there are also different types of oily and dry skin—as described below, there are sixteen types.

Moreover, when used without the guidance of an objective measurement, the terms "oily", "dry" and "sensitive" are subjective, and are susceptible to differing meanings. Additionally, "oily" skin often has a negative connotation. While "very" oily skin should be treated, "slightly" oily skin is desirable. As discussed below, there are two types of oily skin—slightly oily ("O1") and very oily ("O2"). When skin is "slightly oily", there is an occlusive layer of surface lipids that contain naturally occurring antioxidants that forms a protective barrier. This antioxidant rich, lipid-laden barrier effectively serves to keep environmental stressors (e.g., pollutants, allergens, ultraviolet radiation) from injuring the skin and helps skin to retain moisture.

Oily skin is preferable to dry skin. In contrast to oily skin, dry skin is characterized by fewer surface lipids; this results in compromised/reduced skin barrier function, decreased antioxidants (namely Vitamin E), as well as reduced levels of natural moisturizing factor and/or aquaporin activity. Consequently, dry skin is more vulnerable and reactive, and is more rapidly and more strongly irritated.

Similarly, the term "sensitive" is also subjective (in the absence of objective measures) and is misused or overused. As described below, there are multiple subtypes of "sensitive" skin, each requiring distinct treatment regimens in order to accomplish the desired skin change.

The present invention addresses the above shortcomings by changing a person's genetically determined skin type to become the ideal and healthiest skin type which is oily, resistant (not sensitive), non-pigmented (even-toned) and tight (not wrinkle-prone). The methods (i.e., regimens) of the present invention involve treating sixteen specific skin types—each defined based on one or both of an instrumental measurement and/or clinically validated questionnaire in terms of four pairs of clinical characteristics: oily ("O") or dry ("D"); sensitive ("S") or resistant ("R"); pigmented ("P") or non-pigmented ("N"); and wrinkle-prone ("W") or tight ("T").

Figure 1:
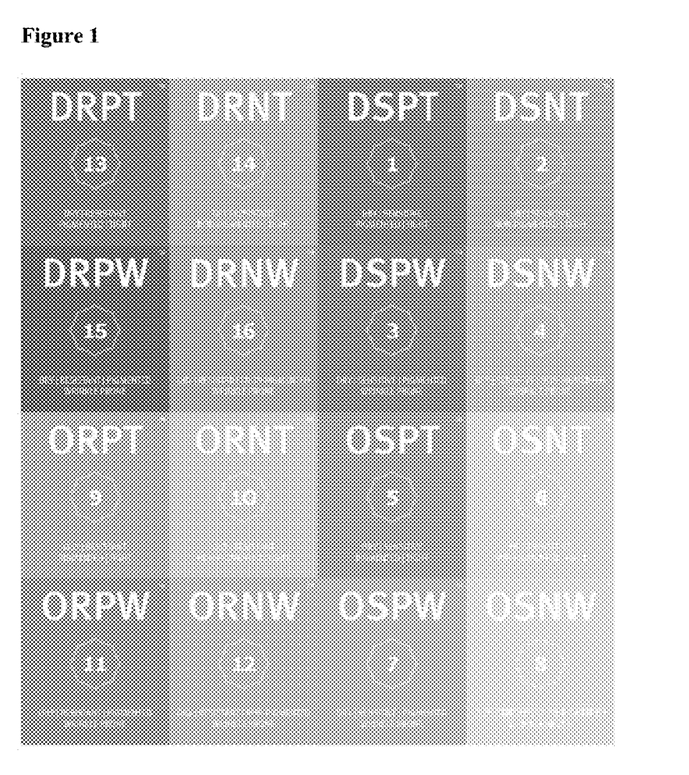
FIGS. 1 and 2 show the four letter sequences, numbers, and colors of the skin types treated by the regimens of the invention.
Figure 2:
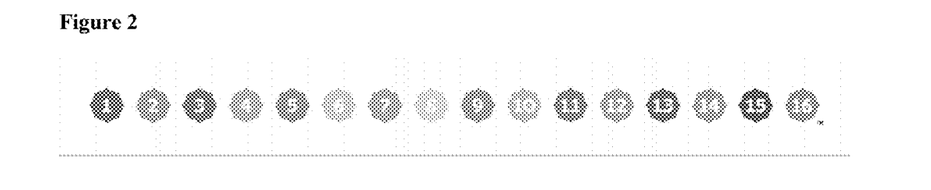

For purposes of ease of patient communication, education, and use, as well as training of, and use by, allied health professionals—the sixteen skin types that are improved/changed by the regimens of the present invention can be abbreviated by four letters or a single number from 1 to 16. This is illustrated in FIG. 1. By way of non-limiting example, ORNT skin may be referred to as skin type 10. Additionally, in certain embodiments, the products used in practicing a regimen of the present invention are labeled with a number, or a four-letter sequence, which is displayed on a background of one of sixteen colors.

The background color with number or four-letter sequence are, in especially preferred embodiments, displayed within a closed geometric shape, preferably a scalloped octagon.

SUMMARY OF THE INVENTION

Methods of improving (i.e., changing) the skin of a patient or consumer who has one of the following skin types: O2RNT, OSPT; OSNT; OSPW; OSNW; ORPT; ORPW; ORNW; DSPT; DSNT; DSPW; DSNW; DRPT; DRNT; DRPW; and DRNW, by changing the skin type to the ideal O1RNT Skin Type. Within these methods, the patient or consumer may have very oily (O2) or slightly oily (O1). Accordingly, in other embodiments, the very oily (O2) skin types are changed to slightly oily (O1) resistant, non-pigmented, tight skin types and all the dry skin types are changed to O1 RNT—slightly oily, resistant, non-pigmented, tight skin types.

A method of improving the skin of a person with O2 (very oily skin) to O1RNT (slightly oily, resistant, non-pigmented, tight) skin.

A method of improving the skin of a person with dry (D) skin to O1RNT (slightly oily, resistant, non-pigmented, tight) skin.

A method of improving the skin of a person with sensitive (S) skin (a combination of one or more of acne, rosacea, stinging, or contact dermatitis) to O1RNT (slightly oily, resistant, non-pigmented, tight) skin.

A method of improving the skin of a person with pigmented (P) skin (uneven skin tone) to O1RNT (slightly oily, resistant, non-pigmented, tight) skin.

A method of improving the skin of a person with wrinkle-prone (W) skin to O1RNT (slightly oily, resistant, non-pigmented, tight) skin.

In a separate embodiment, a maintenance regimen is followed that maintains slightly oily, resistant, non-pigmented, tight skin (O1RNT).

DETAILED DESCRIPTION OF THE PRESENT INVENTION

There are sixteen human skin types, expressed in terms of four pairs of clinical characteristics, wherein: (a) the first pair is selected from the group of oily ("O") or dry ("D"); (b) the second pair is selected from the group of oily sensitive ("S") or resistant ("R"); (c) the third pair is selected from the group of pigmented ("P") or non-pigmented ("N"); and (d) the fourth pair is selected from the group of wrinkle-prone ("W") or tight ("T").

Each of these clinical characteristics is defined below based on one or both of an instrumental measurement and/or clinically validated questionnaire.

While the skilled artisan will appreciate that the same individual can have different skin types at different points in time—e.g., oily during the summer, but dry during the winter; or pigmented (uneven toned) in the summer, but non-pigmented (even toned) in the winter.

Eight (8) human skin types relate to "oily" skin: oily, sensitive, pigmented, tight ("OSPT"); oily, sensitive, non-pigmented, tight ("OSNT"); oily, sensitive, pigmented, wrinkle-prone ("OSPW"); oily, sensitive, non-pigmented, wrinkle-prone ("OSNW"); oily, resistant, pigmented, tight ("ORPT"); oily, resistant, non-pigmented, tight ("ORNT"); oily, resistant, pigmented, wrinkle-prone ("ORPW"); oily, resistant, non-pigmented, wrinkle-prone ("ORNW").

A first aspect of the present invention is directed to methods (regimens) for changing seven of the oily skin types—OSPT; OSNT; OSPW; OSNW; ORPT; ORPW; and ORNW—to an oily, resistant, non-pigmented and tight skin type (ORNT).

In preferred embodiments of this aspect of the invention, the skin is changed to an O1RNT type, where O1 (defined more particularly below) represents "slightly" oily.

A second aspect of the invention is directed to achieving a skin type in which the eight oily skin types are not very oily ("O2") skin, but instead are slightly oil ("O1").

The remaining eight (8) human skin types relate to "dry" skin: dry, sensitive, pigmented, tight ("DSPT"); dry, sensitive, non-pigmented, tight ("DSNT"); dry, sensitive, pigmented, wrinkle-prone ("DSPW"); dry, sensitive, non-pigmented, wrinkle-prone ("DSNW"); dry, resistant, pigmented, tight ("DRPT"); dry, resistant, non-pigmented, tight ("DRNT"); dry, resistant, pigmented, wrinkle-prone ("DRPW"); dry, resistant, non-pigmented, wrinkle-prone ("DRNW").

A third aspect of the present invention is directed to methods (regimens) for changing the eight dry skin types—DSPT; DSNT; DSPW; DSNW; DRPT; DRNT; DRPW; and DRNW—to one of the 8 oily skin types—preferably oily, resistant, non-pigmented and tight skin type (ORNT), and most preferably, O1RNT.

Eight of the sixteen human skin types are "sensitive" and eight are "resistant". The eight sensitive skin types, in turn, are divided into four types of dry skin—DSPT; DSNT; DSPW; DSNW—and four types of oily skin—OSPT; OSNT; OSPW; OSNW.

A fourth aspect of the invention is directed to methods (regimens) for changing the eight sensitive skin types—DSPT; DSNT; DSPW; DSNW; OSPT; OSNT; OSPW; OSNW—to one of the 8 resistant skin types; preferably an oily, resistant, non-pigmented and tight skin type (ORNT), most preferably, O1RNT.

Seven human skin types are "resistant" but not also oily, non-pigmented and tight—namely, DRPT; DRNT; DRPW; DRNW; ORPT; ORPW; and ORNW.

A fifth aspect of the invention is directed to methods (regimens) for changing these seven resistant skin types to an oily, resistant, non-pigmented and tight skin type (ORNT), preferably O1RNT.

Eight of the sixteen human skin types are "wrinkle-prone"—namely, OSPW; ORPW; OSNW; ORNW; DSPW; DRPW; DSNW; and DRNW.

A sixth aspect of the invention is directed to methods (regimens) for changing these eight wrinkle-prone skin types to one of the tight types preferably an oily, resistant, non-pigmented and tight skin type (ORNT), most preferably ideally O1RNT.

Seven human skin types are "tight" but not also oily, resistant and non-pigmented—namely, OSPT; ORPT; OSNT; DSPT; DRPT; DSNT; and DRNT.

A seventh aspect of the invention is directed to methods (regimens) for changing these seven tight skin types to an oily, resistant, non-pigmented and tight skin type (ORNT), preferably O1RNT.

Eight of the sixteen human skin types are "pigmented"—namely, OSPW; ORPW; DSPW; DRPW; OSPT; ORPT; DSPT; and DRPT.

An eighth aspect of the invention is directed to methods (regimens) for changing these eight pigmented skin types to one of the non-pigmented skin types, preferably an oily, resistant, non-pigmented and tight skin type (ORNT), most preferably O1RNT.

Seven human skin types are "non-pigmented" but not also oily, resistant and tight—namely, OSNT; OSNT; DSNT; DRNT; DSNT; and DRNT.

In certain embodiments of the eighth aspect of the invention, individuals with pigmented skin follow an initial treatment regimen that changes their skin from pigmented to non-pigmented, changing to one of the 8 non-pigmented types, preferably O1RNT. This is followed with a maintenance regimen designed to maintain the non-pigmented skin type by prevention of melanin production. In the event of a recurrence of pigmentation, the initial treatment regimen for the individual's initial pigmented skin type is restarted. Once the skin type has again converted to a non-pigmented skin type, the prescribed regimens and procedures transition back to the individual's non-pigmented skin type maintenance regimen.

A ninth aspect of the invention is directed to methods (regimens) for changing these seven non-pigmented skin types to an oily, resistant, non-pigmented and tight skin type (ORNT), preferably O1RNT.

Clinical Characteristics of 16 Skin Types

As used in the present application, skin is classified as "oily" based on one or more of the following methods: measurement of sebum levels using a Sebumeter® or Sebutape®, or comparable technology (e.g., SebuFix®); observation that the skin appears shiny about twenty minutes after washing; oiliness score on a clinically-validated assessment tool (e.g., self-administered questionnaire which may be administered via on an interactive electronic device (including, virtual reality device), a computing device (including tablet computers), a gaming console, a "smart" mobile phone, or other telecommunication device); a questionnaire that is administered by trained skincare professional (including, preferably, a licensed allied health provider); or visual matching to a validated facial assessment scale by a patient/consumer, a computing device having a imaging system (e.g., video or still camera), or a trained skincare professional); or the level of expression of one or more genes associated with increased sebum production.

There are two degrees of "oiliness"—"O1", representing slightly oily skin; and "O2", representing very oily skin. O1 skin is characterized by an amount of sebum minimally sufficient to create an effective occlusive barrier and limit transepidermal loss. One non-limiting example of such a questionnaire is presented in Table 2 of the Appendix to U.S. application Ser. No. 11/283,511—the parent of the present continuation-in-part application. In that questionnaire, a score between 34-44 represents very oily skin, and a score between 27-33 representing slightly oily skin.

A Sebumeter® is an instrumental device for assessing skin oiliness available from Courage+Khazaka electronic GmbH (Cologne, Germany); it uses matte tape that becomes transparent in relation to the amount of sebum on the surface of the skin or hair. After the tape that has been contacted with skin or hair, the tape is analyzed using a photocell; the amount of light transmission is representative of (i.e., correlated with the degree of) sebum content. See, e.g., S W Youn et al. "Evaluation of facial skin type by sebum secretion: discrepancies between subjective descriptions and sebum secretion," *Skin Res. Technol. Vol.* 8, No. 3, pp. 168-72 (August 2002).

Sebutape® available from CuDerm, Corp. (Dallas, Tex.) is another measurement of skin oiliness. This polymeric film is entrained with air microcavities. One side of the film is coated with a lipid-porous adhesive, which enables the film to be affixed to the skin during the period collection. As sebum reaches the skin surface, it is rapidly absorbed into the film. Air within the microcavities is displaced by sebum. The lipid-filled cavities are transparent to light. Additionally, the sebum output from each follicle forms a defined spot, corresponding in size to the volume of the droplet. See, e.g., A M Kligman et al., "Sebutape: A device for visualizing and measuring human sebaceous secretion," *J. Soc. Cosmet. Chem., Vol.* 37, pp. 369-374 (September/October 1986).

Sebufix® is a third method of measuring skin oiliness. This foil, also available from Courage+Khazka, absorbs sebum from the skin surface within the micropores, showing them as spots in different sizes. (Lateral spread of sebum in the foil is minimized.) The foil is mounted on a Visioscan® camera, allowing qualitative sebum production to be monitored in real time.

In certain preferred embodiments of the invention, in addition to, or in place of the above-described instrumental measurements, "oiliness" is assessed based on the six-item skin oiliness scale (SOS) developed by Baumann, et al., "A Validated Questionnaire for Quantifying Skin Oiliness", *Journal of Cosmetics, Dermatological Sciences and Applications*, Vol. 4, pp. 78-84 (2014).

Oiliness can also be assessed based on the expression level of one or more genes associated with sebaceous gland activity (i.e., sebum production).

Dry skin is characterized by impaired skin barrier function, reduced levels of natural moisturizing factor, low level of aquaporin activity and/or decreased sebum production.

For purposes of practicing the methods of the present invention, skin is classified as "dry" based on or more of the following: instrumental measurement of hydration level of the skin surface (stratum corneum), also expressed as transepidermal water loss, using, preferably by using a Corneometer® or Tewameter® (both available from Courage+ Khazaka Electronics GmbH); observation during a physical examination by an allied health professional that the patient's skin feels rough or coarse; human visual or computer image analysis of skin roughness, also known in the art as topographic analysis of skin texture; or expression level of gene(s) associated with skin barrier function, including, but not limited to, a gene that codes for one or more of: filaggrin; 3-hydroxy-3-methylglutaryl coenzyme A (HMG-CoA) reductase; a sterol regulatory element-binding protein (SREBP), such as SREBP-2; a gene that plays a role in ceramide synthesis, such as serine palmitoyltransferase; a gene that plays a role in fatty acid synthesis, such as ALOX15B (Arachidonate 15-lipoxygenaseor INSIG1 (insulin induced-gene-1 protein).

Skin can be assigned a clinical characteristic of "dry" based on the oily/dry score in clinically-validated questionnaire, a non-limiting example of which is Table 2 of the Appendix of the parent to the present application, in which a score between 17-26 represents slightly dry skin, and a score between 11-16 represents very dry skin.

Skin is "sensitive" for purposes of treatment in accordance with the methods of the present invention based on one or more of the following: patient self-reported history of one or more of acne, rosacea, stinging, contact or irritant dermatitis (from use of skincare products containing one or more ingredients that elicit an allergic response); observation of one or more acne lesions, comedones, macules, papules or pustules or erythema during physical examination by an allied health professional; a positive response to either a lactic acid stinging test or a patch test for contact or irritant dermatitis; measurement of histamine release (e.g., by cutaneous microdialysis) or inflammatory cytokine levels such as IL-1, IL-6, IL-8, IFN-gamma and TNF-alpha; an assessment of diffuse redness (e.g., from vasodilation) or erythema using a clinically-validated assessment scale that measures the shade of redness and the percent of facial surface area that is affected; spectrophometric analysis of skin redness/ erythema; computer image analysis of macule/papule/pustule/comedone number and/or lesion count; expression level of a gene or a single-nucleotide polymorphism (SNP) associated with rosacea, such SNP rs763035 and SNP rs111314066; a gene associated with one or more of acne, stinging sensation upon application of a low pH substance, or susceptibility to contact or irritant dermatitis; a gene associated with control of mast cell mediated histamine release and regulation of pro-inflammatory cytokines such as IL-1, IL-6, IL-8, IFN-gamma and TNF-alpha; a gene associated with activation and control of the arachidonic acid cascade and prostaglandin production.

Acne and rosacea are different subtypes of sensitive. Additionally, as noted above an individual can have sensitive skin based on experiencing (i) stinging or (ii) allergic reaction when an ingredient is applied, each as defined below.

For purposes of the present invention, an individual has "allergic", sensitive skin if s/he experiences contact dermatitis, by which is meant an allergic or irritant reaction when her/his skin is contacted with one of the ingredients listed in Table B at the end of the Specification.

For purposes of the present invention, an individual has "stinging", sensitive skin if s/he experiences stinging when her/his skin is contacted with one of the ingredients listed in Table C at the end of the Specification.

In certain embodiments of the invention, an individual with sensitive acne skin may have a combination of one or more of acne, rosacea, stinging, or contact dermatitis.

An individual with acne or rosacea and (a) stinging skin, (b) allergic skin, or (c) stinging and allergic skin, would have "sensitive" skin, and would follow an acne or rosacea regimen for her/his skin type, which would be modified to eliminate use of a product that contains stinging ingredient(s) listed on Table B or allergen(s)/irritant(s) on Table C.

In the regimens described below, if an individual has sensitive skin—due to stinging or contact dermatitis—but does not have acne or rosacea, that individual would follow the sensitive rosacea regimen for her/his specific skin type as described below, but would not use a product that contains ingredient(s) listed on Tables B (stinging) or C (contact dermatitis) that causes, respectively, the stinging or contact dermatitis.

Skin that is not "sensitive" according to the above testing methods is "resistant".

Skin is "wrinkle-prone" for purposes of treatment in accordance with the methods of the present invention based on one or more of the following: clinical photography and computer image analysis of depth, width, and/or length of wrinkles/fine lines; expression level of one or more genes associated with collagen, elastin, or hyaluronic acid such as the genes that control production of the enzymes collagenase, elastase, matrix metalloproteinases and hyaluronidase and the genes that regulate collagen, elastin and hyaluronic acid and extracellular matrix production; assessment of wrinkle/fine lines severity on a clinically-validated assessment tool administered to the patient. Non-limiting examples of clinically-validated assessment tools include the methods disclosed in the following publications: D. Shoshani, "The modified Fitzpatrick Wrinkle Scale: a clinical validated measurement tool for nasolabial wrinkle severity assessment" *Dermatol Surg.* Vol. 34 (Suppl. 1), pp. S85-91 (2008); A. Carruthers et al., "A validated grading scale for crow's feet" *Dermatol Surg.* Vol. 34 (Suppl. 2), pp. S173-S178 (2008); D J Day et al. "The wrinkle severity rating scale: a validation study," *Am J Clin Dermatol, Vol.* 5, pp. 49-52 (2004).

Skin that is not "wrinkle-prone" according to the above testing methods is "tight".

In practicing methods of the present invention, skin is characterized "pigmented" based on one of the following: instrumental analysis with a spectrophotometer or computer imaging analysis of a clinical photograph taken at a specified wavelength; assessment that the skin exhibits uneven color or spots based on a clinically-validated assessment tool or scale (as described above); expression of a gene that controls melanin production, not limiting examples of which include, TYR, DCT and MITF.

Except as discussed immediately below, skin that is not pigmented according to the above testing methods, is designated "non-pigmented".

Formulations Used in Practicing Regimens of Invention

In practicing the regimens of the present invention, an individual uses (applies) at least three separate product types to her/his facial skin on a daily basis: one product cleanses by removing make-up, dead skin cells, oil, dirt, and other pollutants from the skin; a second product that protects the skin from damage caused by environmental stressors (pollutants, allergens, ultraviolet radiation, other skincare products), pathogenic agents (e.g., *Propionibacterium acnes*), the elements (wind, cold, lack of humidity); a third product that repairs or treats one or more of (i) impaired skin barrier, (ii) skin inflammation (acne, rosacea, stinging, or contact dermatitis), (iii) uneven skin tone, and/or (iv) signs of skin aging (wrinkles, lines, thin/fragile skin). Each of these products may be referred to elsewhere in the application by its function—a cleanser, a protectant, or a product that repairs or treats.

In especially preferred embodiments of the invention, the individual uses the at least three product types both in the morning and the evening. In certain embodiments, the individual may use the same product within a product type morning and evening.

In still other regimens, one product may provide two or three of a cleansing, protecting and/or repair/treating function.

The following products can serve both cleansing and repair functions: Salicylic Acid Cleanser; Hydroxyacid Cleanser; Soothing Cleanser; and Benzoyl Peroxide Face and Body Cleanser.

The following products can serve both protecting and repair functions: Brightening Product; Barrier Repair Moisturizer; Soothing Barrier Repair Moisturizer; Soothing Antioxidant Oil; Antioxidant Moisturizer for Dry Skin; Vitamin C Product; Acne Treatment Toner; Retinoid Antimicrobial; Retinoid Skin Lightener; and BP Acne Treatment.

Certain regimens of the present invention used in treating oily skin types employ a Salicylic Acid Cleanser, a composition containing one more surfactants, salicylic acid at a concentration of from 0.5 to 2% wt/wt, and, optionally, but preferably, one or more antimicrobial ingredients, non-limiting examples of which include triclosan and silver. In particularly preferred embodiments, the pH of the Salicylic Acid cleanser is from 2.5 to 4.0. The Salicylic Acid Cleanser does not contain any oils, waxes or butters.

Other regimens of the present invention used in treating oily skin types employ a Non-Foaming Cleanser, by which is also meant low-foaming, and comprised of at least one non-ionic surfactant. Preferably the Non-Foaming Cleanser is in the form of a cream or milk. Non-ionic surfactants suitable for use in Non-Foaming Cleanser include, alcohols, oils, fatty acids, amines and alkanol amides, which can be reacted with ethylene oxide and/or propylene oxide to form ethoxylates, propoxylates, and random and block co-polymers. The Non-Foaming Cleanser does not contain a soap or a charged surfactant (e.g., an anionic sulfate surfactant, such as sodium lauryl).

In one preferred embodiment, the Non-Foaming Cleanser is comprised of Myristoyl/Palmitoyl Oxostearamide/Arachamide MEA, an organic compound corresponding to the formula below:

where m has a value of 14 or 16, and n has a value of 13 or 15, respectively.

Other regimens of the present invention used in treating oily skin types employ a Non-Foaming Cleanser comprised of at least one of: a moisturizing ingredient or humectant, preferably glycerin; a fatty acid, preferably selected from the group consisting of stearic acid or linoleic acid; and oils, preferably, derived from safflower seed, flaxseed oil, argan kernel, macadamia nut.

Still other regimens of the present invention Foaming Cleanser, a product that creates foam or lather when dispensed or rubbed into the skin and gives the consumer/patient a perceived indication that the product is functioning as a cleanser. Foaming Cleansers useful in practicing regimens of the present invention contain one or more charged surfactants, selected from the group of anionic surfactants, cationic surfactants and amphoteric (or zwitterionic) surfactants. These surfactants create foam or suds and have excellent detergency—the ability to suspend and remove oils and debris from the skin. In certain embodiments, the Foaming Cleanser contains an anionic surfactant having a pendant group selected from carboxylic acids, sulfates, sulfonic acids, and phosphoric acid derivatives. Sulfate anionic surfactants include sodium lauryl sulfate (SLS), ammonium lauryl sulfate (ALS), and their ethoxylated derivatives. Sulfonic acid anionic surfactants may be selected from the group of taurates, isethionates, olefin sulfonates, and sulfosuccinates. In certain embodiments, an amphoteric surfactant may be included in the Foaming Cleanser to boost foam.

In other embodiments, the Foaming Cleanser can be a soap—a sodium or potassium salt of long-chain fatty acids.

Importantly, the Foaming Cleanser does not include ingredients that can create an oily or greasy after-feel, including but not limited to lanolin, petrolatum, silicone, oils, butters or other waxy substances.

In regimens of the present invention directed to treatment of dry skin, a Hydroxyacid Cleanser is used, where the hydroxyacid is an alpha-hydroxy acid, preferably glycolic acid, or a polyhydroxy acid, preferably gluconolactone. Preferably, the Hydroxyacid Cleanser has a pH of from 2 to 4. The Hydroxyacid Cleanser does not contain peptides or bioactive proteins or similar ingredients that are denatured or otherwise inactivated at low pH.

In regimens of the present invention directed to treatment of sensitive skin, a Soothing Cleanser is used, which contains one or more anti-inflammatory agents, preferably selected from the group consisting of: argan oil; green tea; allantoin; aloe; chamomile; fever few; niacinamide; Epigallocatechin gallate (EGCG); a glucoside, including Epigallocatechin Gallatyl Glucoside (preferably combined with Propyl Gallate and Gallyl Glucoside (an ingredient blend commercially available under the tradename Unisooth® EG-28 from Unichem), or Rosmarinyl Glucoside, Caffeyl Glucoside, Gallyl Glucoside (an ingredient blend commercially available under the tradename Endothelyol® from Unichem).

In certain embodiments, the Soothing Cleanser contains an agent that (i) suppresses the physiologic response to tumor necrosis factor (TNF), (ii) increases vasoconstriction of cutaneous blood vessels through action not limited to alpha 1 or alpha 2 receptors or beta receptors, (iii) reduces effects mediated by histamine, (iv) suppresses inflammatory cytokine levels, including IL-1, IL-6, IL-8, IFN-gamma, nuclear factor kappa Beta and TNF-alpha, (v) suppresses prostaglandin production, or (vi) suppresses the arachadonic acid cascade. Preferably, the Soothing Cleanser contains one or more of argan oil, safflower oil, macadamia nut oil, or grape seed extract.

The Soothing Cleanser cannot have pH below 3.5, and cannot contain exfoliants (such as hydroxy acids), irritants (such as retinoids) or an ingredient on Table B.

In certain embodiments of the present invention in which the patient/consumer has oily sensitive skin with acne a Benzoyl Peroxide Face and Body Cleanser is used. A Benzoyl Peroxide Face and Body Cleanser contains in the methods of the present invention means a cleansing product that contains benzoyl peroxide at a concentration of from 2.5% to 10%. In certain preferred embodiments, in addition to benzoyl peroxide, the cleanser also contains silver and/or an antimicrobial agent. The Benzoyl Peroxide Face and Body Cleanser cannot contain retinoids or other ingredients known to oxidize when exposed to pro-oxidants.

In certain embodiments of the present invention in which the patient/consumer has sensitive skin, in particular acne, a silver coated/treated textile is used as a pillowcase, facemask, clothing or bed sheeting. The silver coated/treated textile is coated/treated with colloidal silver and, preferably, one or more acne treatment ingredient(s) selected from benzoyl peroxide, clindamycin, erythromycin, polyhydroxy acid, willow bark extract, salicylic acid, resorcinol, resorcinol monoacetate, niacinamide, sulfur, beta carotene, a retinoid (preferably, retinol, tretinoin, adapalene, tazarotene, retinyl palmitate, retinyl linoleate) a tyrosinase inhibitor, a PAR-2 blocker, a lignin peroxidase, or an ingredient that binds Toll-like 2 receptors.

In treating pigmented skin types, a Brightening Product, preferably a serum, a composition containing one or more ingredients that reduce melanin production, inhibit tyrosinase, promote exfoliation, lyse melanosomes, block protease activated receptor 2 (PAR-2) or reduce the appearance of hyperpigmentation, preferably selected from the group consisting of ascorbic acid, resorcinol, hydroquinone, kojic acid, aloesin, arbutin, retinoids, including retinol, licorice extract, soy, niacinamide and derivatives thereof. The Brightening Product does not contain dihydroxyacetone, oil of bergamot, or ingredients that increase melanin production.

Certain sensitive skin types are treated in methods of the present invention with a Non-Comedogenic Light Moisturizer, a topical composition that imparts or attracts moisture to the skin or retains moisture within the skin that preferably contains one or more of glycerin, hyaluronic acid, polysaccharides, free amino acids such as sodium PCA (pyrrolidone carboxylic acid), urea, or sodium, potassium, calcium, and magnesium salts of chlorides, phosphates, and citrates. Importantly, the Non-Comedogenic Light Moisturizer, does not contain an ingredient listed in Table A, at the end of the specification.

Certain sensitive skin types are treated in methods of the present invention with a Light Antioxidant Moisturizer, a topical composition that imparts or attracts moisture to the skin or retains moisture within the skin, that preferably contains one or more of ascorbic acid, tocopherol acetate, polydatin glucoside (empirical $C_{26}H_{32}O_{13}$, commercially available as Uvaxine®, from Induchem Companies), one or more amino acids that help repair visible UV-induced DNA damage (including a combination of Acetyl Tyrosine, Proline, with Hydrolyzed Vegetable Protein, Adenosine Triphosphate, commercially available as Unirepair®, or the combination of panthenyl triacetate and ethyl linoleate dissolved in oleyl alcohol, commercially available as Uniprotect PT-3®, both from Induchem), green tea, resveratrol, caffeine, coffeeberry, and turmeric, or TLR-7 agonist immunomodulator, such as imiquimod, or other immunomodulator that increases production of cytokines with antiaging activity. The Light Antioxidant Moisturizer cannot contain any waxes, butters or oils (including silicones).

A preferred moisturizer used in regimens to treat dry, sensitive skin is a Soothing Barrier Repair Moisturizer, a topical composition that imparts or attracts moisture to the skin or retains moisture within the skin that preferably one or more of Myristoyl/palmitoyl oxostearamide/arachamide MEA, cholesterol, an essential fatty acid, a ceramide, and/or an anti-inflammatory agent. In certain preferred embodiments, the Soothing Barrier Repair Moisturizer contains one or more anti-inflammatory agents that (i) suppresses the physiologic response to tumor necrosis factor (TNF), (ii) increases vasoconstriction of cutaneous blood vessels through action not limited to alpha 1 or alpha 2 receptors or beta receptors, (iii) reduces effects mediated by histamine, (iv) suppresses inflammatory cytokine levels, including IL-1, IL-6, IL-8, IFN-gamma, nuclear factor kappa Beta and TNF-alpha, (v) suppresses prostaglandin production, or (vi) suppresses the arachadonic acid cascade. Preferably, these anti-inflammatory agents are selected from the group consisting of argan oil, green tea, allantoin, aloe, chamomile, fever few, niacinamide, Unisooth®, EGCG, and Endothelyol®.

The Soothing Barrier Repair Moisturizer cannot have pH below 3.5, and cannot contain exfoliants (such as hydroxy acids), irritants (such as retinoids) or an ingredient listed on Table B.

Certain regimens of the present invention employ a Soothing Antioxidant Oil by which is meant an oil containing linoleic acid (and other fatty acids) that contains one or more anti-inflammatory agents, preferably selected from the group consisting of argan oil, green tea, allantoin, aloe, chamomile, fever few, niacinamide, Unisooth®, Endothelyol®, and EGCG. The Soothing Antioxidant Oil cannot have pH below 3.5, and cannot contain exfoliants (such as hydroxy acids), irritants (such as retinoids) or an ingredient listed on Table B. In preferred embodiments, the Soothing Antioxidant Oil is fragrance and preservative free.

In certain embodiments, the Soothing Antioxidant Oil contains an agent that (i) suppresses the physiologic response to tumor necrosis factor (TNF), (ii) increases vasoconstriction of cutaneous blood vessels through action not limited to alpha 1 or alpha 2 receptors or beta receptors, (iii) reduces effects mediated by histamine, (iv) suppresses inflammatory cytokine levels, including IL-1, IL-6, IL-8, IFN-gamma, nuclear factor kappa Beta and TNF-alpha, (v) suppresses prostaglandin production, or (vi) suppresses the arachadonic acid cascade.

Preferably, the Soothing Antioxidant Oil contains one or more of argan oil, safflower oil, macadamia nut oil, or grape seed extract.

In certain regimens of the present invention an Antioxidant Moisturizer for Dry Skin is used, by which is meant a topical composition that imparts or attracts moisture to the skin or retains moisture within the skin that preferably one or more of green tea, caffeine, coffeeberry, tumeric, resveratrol, glycerin, argan oil, almond oil, ascorbic acid or a derivative thereof, tocopherol acetate, Uvaxine®, Unirepair®, Unprotect® (each described above), green tea, resveratrol, caffeine, coffeeberry, and turmeric, or TLR-7 agonist immunomodulators such as imiquimod, or other immunomodulators that increase production of cytokines with antiaging activity in addition to barrier repair ingredients such as Myristoyl/palmitoyl oxostearamide/arachamide MEA, cholesterol, stearic acid, or a ceramide.

The Antioxidant Moisturizer for Dry Skin cannot contain alcohols or pro-oxidants, e.g., peroxides.

The Vitamin C Product, preferably a serum, as used in the practicing the methods of the present invention means ascorbic acid, or a derivative thereof, including, for example, ascorbyl phosphate. Preferably, the Vitamin C Product contains ascorbic acid, and has a pH of less than 2.6. The Vitamin C product must be manufactured under conditions that limit exposure to oxygen and light, and is preferably packaged in an airless, light-resistant, preferably opaque, container (i.e., an airless pump).

Certain sensitive skin types are treated with an Anti-Redness Product, preferably a serum, a topical composition that includes one or more anti-inflammatory or antibiotic ingredient preferably selected from the group of doxycycline, azelaic acid, metronidazole diaminodiphenyl sulfone (also known as dapsone) sulfur, selenium sulfide, and zinc and other anti-inflammatory agents, preferably selected from the group consisting of argan oil, green tea, allantoin, aloe, chamomile, fever few, niacinamide, Unisooth®, Endothelyol®, EGCG, or vasoconstrictive ingredients such as brimonidine or oxymetazoline that block alpha receptors in blood vessels. The Anti-Redness Product does not contain a retinoid, an ingredient on Table B, or a vasodilator.

Skin Lightener for Dry Skin is used in certain regimens of the invention directed to dry pigmented skin types and includes (a) one or more skin lightening ingredients, preferably selected from the group consisting of ascorbic acid and its derivatives (preferably, tetrahexyldecyl ascorbate), resorcinol and its derivatives (preferably, hexyl resorcinol), hydroquinone, kojic acid, aloesin (a C-glycosylated chromone compound found in aloe), arbutin, licorice extract and other ingredients that inhibit tyrosinase, promote exfoliation, lyse melanosomes, block protease activated receptor 2 (PAR-2) (b) one or more skin barrier repair ingredients, preferably selected from the group consisting of fatty acids, stearic acid, cholesterol, ceramides, glycerin, Myristoyl/Palmitoyl Oxostearamide/Arachamide MEA. The Skin Lightener for Dry Skin does not contain bergamot oil or an ingredient that increases melanin production.

Oily pigmented skin types are treated in certain regimens of the present invention with a Skin Lightener for Oily Skin, a topical composition that includes one or more lightening ingredients, preferably selected from the group consisting of ascorbic acid and its derivatives (preferably, tetrahexyldecyl ascorbate), resorcinol and its derivatives (preferably, hexyl resorcinol), hydroquinone, kojic acid, aloesin, arbutin, licorice extract, retinol, tretinoin, adapalene, and tazarotene and other ingredients that inhibit tyrosinase, promote exfoliation, lyse melanosomes, or block protease activated receptor 2 (PAR-2). The Skin Lightener for Oily Skin does not contain bergamot oil or an ingredient that increases melanin production, and does not contain any oils (including silicones), waxes or butters.

Sensitive skin types having acne are treated in certain regimens of the present invention with an Acne Treatment Toner, a topical composition that includes one or more ingredients that reduce the number, severity or recurrence of acne macules, papules, pustules, lesions, ingredients, preferably selected from the group of salicylic acid, sulfur, silver, benzoyl peroxide, resorcinol, clindamycin, erythromycin, tretinoin, triclosan, tazarotene, adapalene, allantoin, and zinc. The Acne Treatment Toner does not contain any ingredient(s) on Table A.

In treating skin types with acne, a BP Acne Treatment is used—namely, a topical composition that benzoyl peroxide in amount that reduces the number, severity or recurrence of acne macules, papules, pustules, lesions; optionally, but preferably this composition includes one or more of silver and/or an antimicrobial agent. The BP Acne Treatment does not contain any ingredient(s) on Table A.

The term Retinoid, as used in the methods of the present invention, means retinol, retinal, retinol esters ($C_2$-$C_{22}$ alkyl esters of retinol, including retinyl palmitate, retinyl acetate, retinyl propionate), retinal, and/or retinoic acid (including all-trans retinoic acid and/or 13-cis-retinoic acid). In preferred embodiments, the Retinoid is retinol, tretinoin, adapalene {6-[3-(1-adamantyl)-4-methoxyphenyl]-2-naphthoic acid}, or tazarotene {ethyl 6-[2-(4,4-dimethylthiochroman-6-yl)-ethynyl]nicotinate}, each at a dose of less than 2%. The Retinoid does not contain an oxidizing ingredient that would inactivate (reduce the bioactivity of) the retinoid. The Retinoid containing product must be manufactured under conditions that limit exposure to oxygen and light, and is preferably packaged in an airless, light-resistant, preferably opaque, container (i.e., an airless pump).

Retinoid Antimicrobial as used practicing certain regimens of the present invention means a topical composition that includes (a) a retinoid, preferably selected from the group of retinol, tretinoin, adapalene, and tazarotene and (b) an antimicrobial agent, preferably, silver, clindamycin, benzoyl peroxide, dapsone, or erythromycin. The Retinoid Antimicrobial does not contain an oxidizing ingredient that would inactivate (reduce the bioactivity of) the retinoid. The Retinoid Antimicrobial must be manufactured under conditions that limit exposure to oxygen and light, and is preferably packaged in an airless, light-resistant, preferably opaque, container (i.e., an airless pump).

Retinoid Skin Lightener as used practicing certain regimens means (a) a retinoid preferably selected from the group of retinol, tretinoin, adapalene, and tazarotene and (b) at least one skin lightening ingredient, preferably selected from the group consisting of ascorbic acid and its derivatives (preferably, tetrahexyldecyl ascorbate), resorcinol and its derivatives (preferably, hexyl resorcinol), hydroquinone, kojic acid, aloesin, arbutin, and licorice extract. The Retinoid Skin Lightener does not contain an oxidizing ingredient that would inactivate (reduce the bioactivity of) the retinoid. The Retinoid Skin Lightener must be manufactured under conditions that limit exposure to oxygen and light, and is preferably packaged in an airless, light-resistant, preferably opaque, container (i.e., an airless pump).

Anti-Aging Retinoid Alternative as used in the methods of the present invention means a topical composition that does not include any retinoid, but contains one or more growth factors, stem cells, estrogen receptor agonists, cytokines, DMAE, niacinamide, glucosamine, a TLR-7 agonist such as imiquimod, N-acetyl glucosamine-6-phosphate (NovHyal® from Induchem), DNA repair ingredients (described above), and antioxidants such as, ascorbic acid, idebenone, or ingredients that attract macrophages, plasmacytoid dendritic cells, or other immune cells to the skin to serve a reparative function, or ingredients that activate the retinoic acid (RAR) receptor or stimulate genes that produce collagen, elastin, or hyaluronic acid.

A Non-Comedogenic Light Facial Sunscreen is used in treating certain sensitive skin types according to the methods the present invention. This facial moisturizer contains has an SPF of at least 15, preferably at least 30, and does not contain any ingredients in Table 1 but does contain (a) one or more of (i) a chemical sunscreen that absorbs UVA radiation, preferably, avobenzone or ecamsule (USAN Mexoryl), or (ii) a particulate sunscreen (also referred to as physical or mineral sunscreen) that blocks UVA selected from the group of zinc oxide or titanium dioxide), (b) at least one chemical sunscreen that absorbs UVB radiation, preferably selected from salicylates (octisalate or homosalate) or cinnamates (octylmethoxycinnamate and cinoxate); (c) optionally a sunscreen that absorbs shorter-wavelength UVA, namely a benzophenone selected from the group of oxybenzone and sulisobenzone. The Non-Comedogenic Light Facial Sunscreen does not contain any ingredient listed on Table A.

A Physical Facial Sunscreen—a sunscreen that contains one or both of zinc oxide and/or titanium dioxide—may be used as part of many of the regimens of the present invention, and is preferably used in regimens directed to the treatment of oily skin types. In the latter, the sunscreen is not used in combination with avobenzone. The Physical Facial Sunscreen does not contain any chemical sunscreens.

Regimens of the Invention

The present invention is directed to regimens for improving (i.e., changing) the skin of a patient or consumer who has one of the following skin types to the "ideal" O1RNT skin: O2RNT, OSPT; OSNT; OSPW; OSNW; ORPT; ORPW; ORNW; DSPT; DSNT; DSPW; DSNW; DRPT; DRNT; DRPW; and DRNW.

One aspect of the methods of the present invention is to change the skin of a patient or consumer with very oily (O2) skin to slightly oily (O1), resistant, non-pigmented, tight skin.

Another aspect of the methods of the present invention is to change the skin of a patient or consumer with dry skin to O1RNT—slightly oily (O1), resistant, non-pigmented, tight skin.

The specific methods for each of the skin types to be changed to O1RNT are set out below with reference to the formulations in the immediately preceding section.

In describing the regimens, the phrase "prescribed" is to be understood to mean that the patient applies the products in the regimen to her/his facial skin in the manner directed.

The regimen formulations provide non-limiting examples of the three product types—cleansing, protecting, repairing—that can be used in practicing the methods of the present invention—namely, for individuals who do not have O1RNT changing their skin to that ideal skin type; and in the case of individuals having O1RNT maintaining those desired skin characteristics.

In certain of these regimens, one product may provide two or three of a cleansing, protecting and/or repair/treating function. For example, in the DRNT regimen, the evening regimen includes use of Barrier Repair Moisturizer that both protects and repairs.

In practicing the regimens of the present invention, it is preferred that the morning regimen includes a product that protects the skin from UV radiation and that the evening regimen includes a cleansing product.

Lastly, it is to be understood that the methods/regimens of the present invention involve a step of clinically determining whether skin is oily, dry, sensitive, pigmented or wrinkle-prone by using one or more of the instrumental measurements, gene expression tests, or validated assessment tools/scales discussed above.

A patient with DSPT with acne is prescribed a morning regimen of Hydroxyacid Cleanser, Acne Treatment Toner, Soothing Barrier Repair Moisturizer, Non-Comedogenic Light Facial Sunscreen and an evening regimen of Non-Foaming Cleanser, Soothing Barrier Repair Moisturizer, Retinoid Antimicrobial.

A patient with DSPT with rosacea is prescribed a morning regimen of Soothing Cleanser, Soothing Antioxidant Oil, Soothing Barrier Repair Moisturizer, Physical Facial Sunscreen and an evening regimen of Soothing Cleanser, Soothing Antioxidant Oil, Soothing Barrier Repair Moisturizer, Skin Lightener for Dry Skin.

A patient with DSNT with acne is prescribed a morning regimen of Hydroxyacid Cleanser, Acne Treatment Toner, Soothing Barrier Repair Moisturizer, Non-Comedogenic Light Facial Sunscreen and an evening regimen of Non-Foaming Cleanser, Acne Treatment Toner, Soothing Barrier Repair Moisturizer, Retinoid Antimicrobial. In place of the Retinoid Antimicrobial, a Retinoid may be used.

A patient with DSNT with rosacea is prescribed a morning regimen of Soothing Cleanser, Soothing Antioxidant Oil, Soothing Barrier Repair Moisturizer, Non-Comedogenic Light Facial Sunscreen and an evening regimen of Soothing Cleanser, Soothing Antioxidant Oil, Soothing Barrier Repair Moisturizer.

A patient with DSPW with acne is prescribed a morning regimen of Hydroxyacid Cleanser, Acne Treatment Toner, Skin Lightener for Dry Skin, Non-Comedogenic Light Facial Sunscreen and an evening regimen of Non-Foaming Cleanser, Acne Treatment Toner, Soothing Barrier Repair Moisturizer, Retinoid Antimicrobial. In place of the Retinoid Antimicrobial, a Retinoid may be used.

A patient with DSPW with rosacea is prescribed a morning regimen of Soothing Cleanser, Skin Lightener for Dry Skin, Soothing Barrier Repair Moisturizer, Physical Facial Sunscreen and an evening regimen of Non-Foaming Cleanser, Soothing Barrier Repair Moisturizer, Soothing Antioxidant Oil, Anti-Aging Retinoid Alternative. After approximately one month, the patient's regiment is changed from Anti-Aging Retinoid Alternative to a retinoid, preferably retinol.

A patient with DSNW with acne is prescribed a morning regimen of Hydroxyacid Cleanser, Acne Treatment Toner, Soothing Barrier Repair Moisturizer, Non-Comedogenic Light Facial Sunscreen and an evening regimen of Non-Foaming Cleanser, Acne Treatment Toner, Soothing Barrier Repair Moisturizer, Retinoid Antimicrobial.

A patient with DSNW with rosacea is prescribed a morning regimen of Soothing Cleanser, Soothing Antioxidant Oil, Soothing Barrier Repair Moisturizer, Non-Comedogenic Light Facial Sunscreen and an evening regimen of Non-Foaming Cleanser, Soothing Barrier Repair Moisturizer, Soothing Antioxidant Oil, Anti-Aging Retinoid Alternative.

A patient with OSPT with acne is prescribed a morning regimen of Salicylic Acid Cleanser, BP Acne Treatment, Skin Lightener for Oily Skin, Non-Comedogenic Light Facial Sunscreen and an evening regimen of Salicylic Acid Cleanser, Acne Treatment Toner, Non-Comedogenic Light Moisturizer, Retinoid Antimicrobial.

A patient with OSPT with rosacea is prescribed a morning regimen of Salicylic Acid Cleanser, Anti-Redness Product, preferably a serum, Non-Comedogenic Light Facial Sunscreen and an evening regimen of Foaming Cleanser, Anti-Redness Product, preferably a serum, Retinoid Skin Lightener.

A patient with OSNT with acne is prescribed a morning regimen of Salicylic Acid Cleanser, Acne Treatment Toner, Non-Comedogenic Light Facial Sunscreen and an evening regimen of Salicylic Acid Cleanser, Acne Treatment Toner, Non-Comedogenic Light Moisturizer, Retinoid Antimicrobial.

A patient with OSNT with rosacea is prescribed a morning regimen of Salicylic Acid Cleanser, Anti-Redness Product, preferably a serum, Non-Comedogenic Light Facial Sunscreen and an evening regimen of Foaming Cleanser, Anti-Redness Product, preferably a serum, Light Antioxidant Moisturizer.

A patient with OSPW with acne is prescribed a morning regimen of Salicylic Acid Cleanser, Acne Treatment Toner, Skin Lightener for Oily Skin, Non-Comedogenic Light Facial Sunscreen and an evening regimen of Salicylic Acid Cleanser, Non-Comedogenic Light Moisturizer, Retinoid Antimicrobial. Vitamin C, for example in Vitamin C Product, preferably a serum, may be added to the regimen after acne clears.

A patient with OSPW with rosacea is prescribed a morning regimen of Salicylic Acid Cleanser, Anti-Redness Product, preferably a serum, Non-Comedogenic Light Facial Sunscreen and an evening regimen of Foaming Cleanser, Anti-Redness Product, preferably a serum, Anti-Aging Retinoid Alternative. After approximately one month, the patient's regiment is changed from Anti-Aging Retinoid Alternative to a retinoid, preferably retinol.

A patient with OSNW with acne is prescribed a morning regimen of Salicylic Acid Cleanser, Acne Treatment Toner, Vitamin C Product, preferably a serum, Non-Comedogenic Light Facial Sunscreen and an evening regimen of Salicylic Acid Cleanser, Acne Treatment Toner, Light Antioxidant Moisturizer, Retinoid Antimicrobial.

A patient with OSNW with rosacea is prescribed a morning regimen of Salicylic Acid Cleanser, Anti-Redness Product, preferably a serum, Non-Comedogenic Light Facial Sunscreen and an evening regimen of Foaming Cleanser, Anti-Redness Product, preferably a serum, Anti-Aging Retinoid Alternative. After approximately one month, the patient's regiment is changed from Anti-Aging Retinoid Alternative to a retinoid, preferably retinol.

A patient with ORPT is prescribed a morning regimen of Salicylic Acid Cleanser, Skin Lightener for Oily Skin, Non-Comedogenic Light Facial Sunscreen and an evening regimen of Foaming Cleanser, Light Antioxidant Moisturizer, Retinoid Skin Lightener. In place of the Retinoid Antimicrobial, a Retinoid may be used.

A patient with ORNT is prescribed a morning regimen of Salicylic Acid Cleanser, Non-Comedogenic Light Facial Sunscreen and an evening regimen of Foaming Cleanser, Light Antioxidant Moisturizer.

A patient with ORPW is prescribed a morning regimen of Salicylic Acid Cleanser, Skin Lightener for Oily Skin, Non-Comedogenic Light Facial Sunscreen and an evening regimen of Foaming Cleanser, Vitamin C Product, preferably a serum, Anti-Aging Retinoid Alternative, Retinoid Skin Lightener. In place of the Retinoid Antimicrobial, a Retinoid may be used.

A patient with ORNW is prescribed a morning regimen of Salicylic Acid Cleanser, Vitamin C Product, preferably a serum, Non-Comedogenic Light Facial Sunscreen and an evening regimen of Foaming Cleanser, Anti-Aging Retinoid Alternative, Retinoid.

A patient with DRPT is prescribed a morning regimen of Hydroxyacid Cleanser, Skin Lightener for Dry Skin, Barrier Repair Moisturizer, Physical Facial Sunscreen and an evening regimen of Non-Foaming Cleanser, Barrier Repair Moisturizer, Retinoid Skin Lightener.

A patient with DRNT is prescribed a morning regimen of Non-Foaming Cleanser, Barrier Repair Moisturizer, Physical Facial Sunscreen and an evening regimen of Non-Foaming Cleanser, Barrier Repair Moisturizer.

A patient with DRPW is prescribed a morning regimen of Hydroxyacid Cleanser, Skin Lightener for Dry Skin, Vitamin C Moisturizer, Physical Facial Sunscreen and an evening regimen of Non-Foaming Cleanser, Barrier Repair Moisturizer, Retinoid, Anti-Aging Retinoid Alternative.

A patient with DRNW is prescribed a morning regimen of Hydroxyacid Cleanser, Vitamin C Moisturizer, Barrier Repair Moisturizer, Physical Facial Sunscreen and an evening regimen of Non-Foaming Cleanser, Barrier Repair Moisturizer, Retinoid, Anti-Aging Retinoid Alternative.

Improving (i.e., changing) the skin of a patient/consumer to ORNT, preferably O1RNT, in accordance with the regimens of the present invention typically takes 12-16 weeks of following (i.e., using) the prescribed regimen morning and night, as well as continued use of the regimen after ORNT, more preferably O1RNT, is achieved. The regimens change each of: (i) oily skin to dry skin; and, more preferably, very oily skin to slightly oily skin; (ii) sensitive skin to resistant skin; (iii) pigmented skin to non-pigmented skin; and (iv) wrinkle-prone skin to tight skin. In cases where an individual starts a regimen with the desired clinical characteristic—oily, resistant, non-pigmented and tight skin—that desired characteristic is maintained.

It will be appreciated that during the course of following the regimen, one or more characteristics may change (improve) before others. By way of a first non-limiting example, an OSPT patient may first change to OSNT and thereafter to ORNT. As a second non-limiting example, the skin of a DSPW consumer may become OSPW, and then OSNT before becoming ORNT.

TABLE A

Pore-Clogging Ingredients

Acetylated Lanolin, Acetylated Lanolin Alcohol, Algae Extract, Algin, Almond Oil, Anhydrous Lanolin, Apricot Kernel Oil, Arachidic Acid, Ascorbyl Palmitate, Avocado Oil, Azulene, BHA, Beeswax, Benzaldehyde, Benzoic Acid, Beta Carotene, Bubussa Oil, Butyl Stearate, Butylated Hydroxyanisole (BHA), Butylene Glycol, Cajeput Oil, *Calendula*, Camphor, Candelilla Wax, Capric Acid, Caprylic Acid, Carbomer 940, Carnuba Wax, Carotene, Carrageenan, Castor Oil, Cetearyl Alcohol, Cetyl Alcohol, Chamomile, Chaulomoogra Oil, Cocoa Butter, Coconut Butter, Coconut Oil, Colloidal Sulfur, Corn Oil, Cotton Seed Oil, Crisco, Synthetic Dyes, (Especially, D&C Red #S 3, 4, 6, 7, 9, 17, 19, 21, 27, 230, 33, 36, 40), Decyl Oleate, Dimethicone, Dioctyl Succinate, Disodium Monooleamido, Peg 2-Sulfosuccinate, Emulsifying Wax Nf, Ethoxylated Lanolin, Ethylhexyl Palmitate, Evening Primrose Oil, Glyceryl Stearate Glyceryl Tricapylo/Caprate, Glyceryl-3-Diisostearate, Hexadecyl Alcohol, Hexylene Glycol, Hydrogenated Castor Oil, Hydrogenated Vegetable Oil, Hydroxypropylcellulose, Isocetyl Stearate, Isodecyl Oleate, Isopropyl Isosterate, Isopropyl Myristate, Isopropyl Palmitate, Isostearyl Isostearate, Isostearyl Neopentanoate, Jojoba Oil, Lanolin Alcohol, Lanolin Oil, Lanolin Wax, Laureth 23, Laureth 4, Lauric Acid, Lithium Stearate, Magnesium Stearate, Menthyl Anthranilate, Mink Oil, Myristic Acid, Myristyl Lactate, Myristyl Myristate, Octyl Palmitate, Octyl Stearate, Oleth-3, Oleth-10, Oleyl Alcohol, Olive Oil, Peg 100 Distearate, Peg 100 Stearate, Peg 150 Distearate, Peg 16 Lanolin, Peg 20 Stearate, Peg 200 Dilaurate, Peg 8 Stearate, PG Caprylate/Caprate, PG Dipelargonate, PG Monostearate, Ppg 2 Myristyl Propionate, Palmitic Acid, Peanut Oil, Pentarythrital Tetra Isostearate, PG Dicaprylate/Caprate, PG Dipelargonate, Polyethylene Glycol (Peg 400), Polyethylene Glycol 300, Polyglyceryl-3-Diisostearate, Potassium Chloride, Propylene Glycol Monostearate, Red Algae, Sandelwood Seed Oil, Sesame Oil, Shark Liver Oil, Simethicone, Sodium Chloride (Salt), Sodium Laureth Sulfate, Sodium Lauryl Sulfate, Solulan 16, Sorbitan Laurate, Sorbitan Oleate, Soybean Oil, Squalane, Steareth 10, Steareth 2, Steareth 20, Stearic Acid, Stearic Acid Tea, Stearyl Alcohol, Stearyl Heptanoate, Sulfated Castor Oil, Sulfated Jojoba Oil, Syearyl Heptanoate, Talc, Triethanolamine, Vitamin A Palmitate, Wheat Germ Glyceride/Oil, and Xylene

TABLE B

Ingredients that Cause Stinging Skin Sensitivity

Alcohol
Azelaic acid
Avobenzone
Benzoic acid
Capsaicin
*Eucalyptus* oil
Fragrance
Glycolic acid
Lactic Acid
Menthol
Peppermint
Salicylic acid
Sorbic Acid
Vitamin C
Witch hazel

TABLE C

Ingredients that Can Cause Allergic Skin Sensitivity

2,5 Diaminotoluene Sulfate
2,6-Ditert-butyl-4-cresol (BHT)
2-Ethylhexyl-4-dimethylaminobenzoate (Padimate O)
2-Ethylhexyl-4-methoxycinnamate
2-Hydroxy-4-methoxy-4-methylbenzophenone (Mexenone)
2-Hydroxy-4-methoxy-benzophenon-5-sulfonic acid (Sulisobenzone)
2-Hydroxy-4-methoxybenzophenone
2-Nitro-P-Phenylenediamine
2-tert-Butyl-4-methoxyphenol (BHA)
3-(4-Methylbenzyliden)camphor

TABLE C-continued

Ingredients that Can Cause Allergic Skin Sensitivity

3-Aminophenol Hydroquinone
4-Aminobenzoic acid (PABA)
4-Aminophenol

TABLE C-continued

Ingredients that Can Cause Allergic Skin Sensitivity

4-Chloro-3-cresol (PCMC)
4-tert-Butyl-4'-methoxydibenzoylmethane (Avobenzone)
Ammonium Persulfate
Ammonium Thioglycolate
*Angelica*
*Arnica*
Balsam of Peru (myroxylon pereirae)
Beeswax
Benzoic Acid
Benzophenone-3 (oxybenzone)
Benzyl Alcohol
Benzyl alcohol
Benzyl salicylate
Bladderwrack
Catnip
*Centella assiatica*
Cetyl alcohol
Chamomile
Chloracetamide
Chlorhexidine digluconate
Cocamide DEA
Cocamidopropyl Betaine
Colophony (rosin)
Compositae Mix
Coriander
Cucumber
Di-alpha-tocopherol acetate (Vitamin E)
Dog rose hips
*Echinacea*
Euxyl K 400 (Methyldibromo-glutaronitrile-phenoxyethanol)
Formaldehyde
Formaldehyde Releasing Preservatives (FRPs): Quaternium 15;

TABLE C-continued

Ingredients that Can Cause Allergic Skin Sensitivity

Imidazolidinyl Urea
Diazolidinyl Urea; Bromonitropropane diol; DMDM Hydantoin
*Gingko*
Glyceryl Thioglycolate
Glyceryl Thioglycolate
Goldenseal
Green tea
Homomenthylsalicylate (Homosalate)
Hops
Hydrogen Peroxide
Isoamyl-p-methoxycinnamate
Isopropyl myristate
Kelp
Lanolin alcohol
Lavender
Licorice
Marigold
Methoxycinnamate
Methyl Methacrylate
Methylchloroisothiazolone (MCI)
Octyl salicylate (Octisalate)
Parabens
Para-phenylenediamine
Phenylbenzimidazol-5-sulfonic acid
Potassium Dichromate
Propolis
Propyl gallate
Propylene Glycol
P-Tert-Butylphenol Formaldehyde Resin
Resorcinol
Rosemary
Sage
Sesquiterpene Lactone
Sodium Benzoate
Sorbic Acid
Sorbitan monooleate
Sorbitan sesquioleate
St. John's wort
Stearyl alcohol
Tea Tree Oil
tert-Butylhydroquinone
Toluenesulphonamide Formaldehyde Resin (tosylamide)
Triclosan
Triethanolamine
Witch hazel
Ylang Ylang Oil

The invention claimed is:

1. A method of improving the skin of an individual with oily, sensitive, pigmented, wrinkle-prone skin, by changing the individual's skin to oily, resistant, non-pigmented, tight skin, wherein
   (a) the individual having oily, sensitive, pigmented, wrinkle-prone skin has acne, and uses a morning regimen of Salicylic Acid Cleanser, Acne Treatment Toner, Skin Lightener for Oily Skin, and Non-Comedogenic Light Facial Sunscreen; and uses an evening regimen of Salicylic Acid Cleanser, Non-Comedogenic Light Moisturizer, and Retinoid or Retinoid Antimicrobial, and, optionally, sleeps on a silver coated textile pillowcase; and
   (b) the individual having oily, sensitive, pigmented, wrinkle-prone skin has rosacea, and uses a morning regimen of Salicylic Acid Cleanser, Anti-Redness Product, Non-Comedogenic Light Facial Sunscreen; and uses an evening regimen of Foaming Cleanser, Anti-Redness Product, and Anti-Aging Retinoid Alternative.

2. The method of claim 1 wherein the evening regimen for the individual having oily, sensitive, pigmented, wrinkle-prone skin and rosacea is modified after four weeks by (a) adding a Retinoid to the regimen or (b) replacing the Anti-Aging Retinoid Alternative with a Retinoid.

3. A method of improving the skin of an individual with dry, sensitive, pigmented, wrinkle-prone skin, by changing the individual's skin to oily, resistant, non-pigmented, tight skin, wherein
   (a) the individual having dry, sensitive, pigmented, wrinkle-prone skin has acne, and uses a morning regimen of Hydroxyacid Cleanser, Acne Treatment Toner, Skin Lightener for Dry Skin, and Non-Comedogenic Light Facial Sunscreen ; and uses an evening regimen of Non-Foaming Cleanser, Acne Treatment Toner, Soothing Barrier Repair Moisturizer, and a Retinoid or Retinoid Antimicrobial, and, optionally, sleeps on a silver coated textile pillowcase; and
   (b) the individual having dry, sensitive, pigmented, wrinkle-prone skin, has rosacea, and uses a morning regimen of Soothing Cleanser, Skin Lightener for Dry Skin, Soothing Barrier Repair Moisturizer, and Physical Facial Sunscreen; and uses an evening regimen of Nonfoaming Cleanser, Soothing Barrier Repair Moisturizer, Soothing Antioxidant Oil and Antiaging Retinoid Alternative.

4. The method of claim 3 wherein the morning regimen for the individual having dry, sensitive, pigmented, wrinkle-prone skin and acne is modified after twelve weeks by using a Vitamin C Product in place of the Skin Lightener for Dry Skin for a period of four weeks.

5. The method of claim 4 wherein the morning regimen for the individual having dry, sensitive, pigmented, wrinkle-prone skin and acne is modified further after sixteen weeks if the skin remains pigmented by using the Skin Lightener for Dry Skin in place of the Vitamin C Product, and continuing the use of the Skin Lightener for Dry Skin for no more than twelve weeks.

6. The method of claim 3 wherein the morning regimen for the individual having dry, sensitive, pigmented, wrinkle-prone skin and rosacea is modified after twelve weeks by using a Soothing Antioxidant Oil in place of the Skin Lightener for Dry Skin for a period of four weeks.

7. The method of claim 6 wherein the morning regimen for the individual having dry, sensitive, pigmented, wrinkle-prone skin and rosacea is modified further after sixteen weeks if the skin remains pigmented by using the Skin Lightener for Dry Skin in place of the Soothing Antioxidant Oil, and continuing the use of the Skin Lightener for Dry Skin for no more than twelve weeks.

8. The method of claim 3 wherein the evening regimen for the individual having dry, sensitive, pigmented, wrinkle-prone skin and rosacea is modified after four weeks by (a) adding a Retinoid to the regimen or (b) replacing the Anti-Aging Retinoid Alternative with a Retinoid.

\* \* \* \* \*